(12) United States Patent
Wang et al.

(10) Patent No.: US 10,526,354 B2
(45) Date of Patent: Jan. 7, 2020

(54) ALPHA-SILANE COUPLING AGENT AND APPLICATION THEREOF

(71) Applicant: CHENGDU GUIBAO SCIENCE & TECHNOLOGY CO., LTD., Chengdu (CN)

(72) Inventors: Youzhi Wang, Chengdu (CN); Tianyuan Zhai, Chengdu (CN); Guoyong Che, Chengdu (CN); Daiyu Luo, Chengdu (CN); Ting Xiong, Chengdu (CN)

(73) Assignee: CHENGDU GUIBAO SCIENCE & TECHNOLOGY CO., LTD., Chengdu (CN)

( * ) Notice: Subject to any disclaimer, the term of this patent is extended or adjusted under 35 U.S.C. 154(b) by 0 days.

(21) Appl. No.: 15/758,730

(22) PCT Filed: Jul. 20, 2016

(86) PCT No.: PCT/CN2016/090644
§ 371 (c)(1),
(2) Date: Mar. 9, 2018

(87) PCT Pub. No.: WO2017/041584
PCT Pub. Date: Mar. 16, 2017

(65) Prior Publication Data
US 2019/0031689 A1 Jan. 31, 2019

(30) Foreign Application Priority Data

Sep. 9, 2015 (CN) .......................... 2015 1 0571655

(51) Int. Cl.
*C09J 11/06* (2006.01)
*C07F 7/18* (2006.01)
(52) U.S. Cl.
CPC ............. *C07F 7/1804* (2013.01); *C09J 11/06* (2013.01)
(58) Field of Classification Search
CPC ................................ C09J 11/06; C07F 7/1804
See application file for complete search history.

(56) References Cited

U.S. PATENT DOCUMENTS 5,322,873 A  6/1994  Pohl et al.

FOREIGN PATENT DOCUMENTS

| CN | 1861664 A | 11/2006 |
| CN | 1950458 A | 4/2007 |
| CN | 101072782 A | 11/2007 |
| CN | 105111231 A | 12/2015 |
| JP | 2013114238 A | 6/2013 |
| WO | 2007006491 A2 | 1/2007 |

OTHER PUBLICATIONS

Qingli Zhou et al., α-functional group Silane Coupling Agent, Jiangsu Chemical Industry and Market Seven Daily News, 1984.

*Primary Examiner* — Rebecca L Anderson
(74) *Attorney, Agent, or Firm* — Gokalp Bayramoglu

(57) ABSTRACT

The present invention discloses an α-silane coupling agent and application thereof. The α-silane coupling agent has a structure formula of formula (I):

$$\begin{array}{c} R_4 \\ \diagdown \\ N-CH_2-Si-OR_1 \\ \diagup \quad | \quad \diagdown \\ R_5 \quad OR_3 \quad OR_2 \end{array}$$

$R_1$ is alkyl with 1 to 6 carbon atoms; $R_2$ is alkyl with 1 to 6 carbon atoms; $R_3$ is alkyl with 1 to 6 carbon atoms; $R_4$ or $R_5$ is selected from one of hydrogen, alkyl with 1 to 18 carbon atoms, aryl, benzyl, ester-containing group, carbamido-containing group or heterocyclic alkane; $R_4$ and $R_5$ are the same or different. The α-silane coupling agent is applied to silicone rubber, which can be cured without adding a catalyst, and the curing speed is fast; the α-silane coupling agent has strong reactivity, the surface curing time is less than 2 minutes; and the α-silane coupling agent has good stability, which can be stored stably under conditions at room temperature for 6 months, and does not easily turn yellow.

2 Claims, No Drawings

ALPHA-SILANE COUPLING AGENT AND APPLICATION THEREOF

CROSS REFERENCE TO RELATED APPLICATIONS

This application is the national phase entry of International Application No. PCT/CN2016/090644, filed on Jul. 20, 2016, which is based upon and claims priority to Chinese Patent Application No. 201510571655.9, filed on Sep. 9, 2015.

TECHNICAL FIELD

The present invention relates to the technical field of polymer organic material, and particularly to an α-silane coupling agent and application thereof.

BACKGROUND OF THE INVENTION

Silane coupling agents are a class of organosilicon compounds that contain two different chemical groups in the molecule, which can set up a "molecular bridge" between the interface of inorganic substance and organic substance, and connect two materials with great disparity together to improve the performance of the composite materials and increase the bonding strength. Silane coupling agents are widely used in thermosetting resin composites, thermoplastic resin composites, inorganic fillers, coatings, adhesives, sealants and other fields.

Since the fifties of the last century, thousands of varieties of silane coupling agents have been obtained, including the α-silane coupling agent which has been successfully developed by the Department of Chemistry of Nanjing University in China. Because of the unique structure, the activity of α-silane coupling agent is far greater than that of γ-silane coupling agent, which attracted great interest of scholars from various countries and, a series of studies have been conducted.

Zhou Qingli et al., Department of Chemistry of Nanjing University, published an article titled "α-functional group Silane Coupling Agent" in "Jiangsu Chemical Industry and Market Seven Daily News" in 1984. The properties and synthesis methods of α-functional silane coupling agent were analyzed in detail, the paper argued that α-functional group silane coupling agent can significantly improve the adhesion of one material to another, improve the humidity and heat resistance properties of the sealant; the most important is that when applied to silicone rubber, so that the dosage of organotin catalysts can be significantly reduced and the tack free time of sealant surface can be improved, as to the more active N, N-diethylaminomethyl triethoxysilane (ND-22), the catalyst may not used. According to the research results, the α-silane coupling agents currently used in the market are mainly ND-22, aniline methyl triethoxy silane (ND-42) etc. However, such kind of silane coupling agents are greatly limited in application because of easy discoloration and poor stability.

CN101072782 discloses a piperazine-containing α-silane coupling agent, and compared the stability of the piperazine-containing α-silane coupling agent with the α-silane coupling agent, the result displayed that piperazine-containing α-silane coupling agent has a higher stability, but such kind of silane still have the problem of high activity and easy discoloration.

EU Directive 2009/425/EC, as of Jul. 1, 2010, the EU limits the use of organic tin in all consumer products by less than 0.1%. The dosage of organotin catalysts can be reduced, when the α-silane coupling agents were applied, even may not be used. So the purpose of the present invention is to provide an α-silane coupling agent with adjustable activity and high stability, and when applied to silicone rubber, the tack free time can be significantly reduced, the curing speed and the stability of the sealant can be improved.

SUMMARY OF THE INVENTION

The purpose of the present invention is to provide an alkoxy silane which is moderately reactive and highly stable, on the one hand to adjust the reactivity of the compound by improving the size of the hydrolysis groups, and on the other hand to control the stability of the compound by changing the organic groups on the ammonia.

The present invention is based on the fact that the nitrogen atom of α-aminomethyl silane is located in cyclic groups, such as a morpholine compound or a group that reduces density of the electron cloud, such as carbonyl compounds (ester group, carbamido) etc. On the one hand, the stability of α-aminomethyl silane can be improved, on the other hand, the activity of α-aminomethyl silane coupling agent can be adjusted by using different hydrolysis groups, so that the curing of the silicone rubber can be realized fast and without catalyst.

In order to achieve above technical effect, the present invention adopts the following technical scheme:

An α-silane coupling agent, having a structure formula of formula (I):

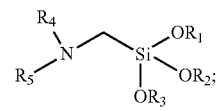

$R_1$ is alkyl with 1 to 6 carbon atoms;
$R_2$ is alkyl with 1 to 6 carbon atoms;
$R_3$ is alkyl with 1 to 6 carbon atoms;
$R_4$ and $R_5$ are the same or different;
$R_4$ or $R_5$ is selected from one of hydrogen, alkyl with 1 to 18 carbon atoms, aryl, benzyl, ester-containing groups, carbamido-containing groups or heterocyclic alkane.

The further technical scheme is: $R_1$, $R_2$ or $R_3$ are one of straight chain alkyl with 1 to 6 carbon atoms, branched alkyl with 1 to 6 carbon atoms, cyclic alkane with 1 to 6 carbon atoms, aromatic alkyl with 1 to 6 carbon atoms or alkyl aryl with 1 to 6 carbon atoms; $R_1$, $R_2$ and $R_3$ are the same or different.

The further technical scheme is: $R_4$ or $R_5$ is an ester-containing group, the group has a structure of formula (II):

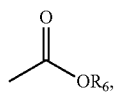

$R_6$ is alkyl with 1 to 18 carbon atoms, the alkyl is selected from one of straight chain alkyl, branched alkyl, cyclic alkane, aromatic alkyl or alkyl aryl.

The further technical scheme is: $R_4$ or $R_5$ is an carbamido-containing group, the group has a structure of formula (III):

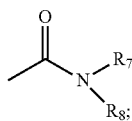

$R_7$ or $R_8$ is selected from one of hydrogen, alkyl with 1 to 18 carbon atoms, aryl or benzyl; the alkyl is one or more of straight chain alkyl, branched alkyl, cyclic alkane, aromatic alkyl or alkyl aryl.

The further technical scheme is: $R_4$ or $R_5$ is a heterocycloalkane-containing group, the group has a structure of formula (IV):

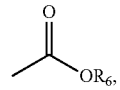

$R_9$ is alkyl with 1 to 12 carbon atoms, the alkyl is one of straight chain alkyl, branched alkyl or cyclic alkane.

The further technical scheme is: $R_9$ is alkyl with 1 to 12 carbon atoms, the alkyl is one of straight chain alkyl, branched alkyl or cyclic alkane; the alkyl chain segment contains one or more of N, O, S, carbonyl or hydroxyl.

The further technical scheme is: $R_1$, $R_2$ or $R_3$ is selected from one of methyl, ethyl, n-propyl, n-butyl, isopropyl or isobutyl.

The further technical scheme is: $R_4$ or $R_5$ is selected from one of hydrogen, methyl, ethyl, n-propyl, n-butyl, isopropyl, isobutyl, phenyl, benzyl, ester group, carbamido or heterocyclic alkane.

The further technical scheme is: $R_6$ is selected from one of methyl, ethyl, propyl, butyl, isopropyl, isobutyl or benzyl.

The further technical scheme is: $R_7$ or $R_5$ is selected from one of hydrogen, methyl, ethyl, n-propyl, n-butyl, isopropyl or isobutyl.

The further technical scheme is: $R_4$ or $R_5$ is selected from one of pyrrole, imidazole, oxazole, piperidine, morpholine or oxazine.

The present invention also provides the application of the α-silane coupling agent in the sealant curing process.

The present invention is further described below.

An α-silane coupling agent, having a structure formula of formula (I):

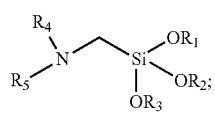

$R_1$ is alkyl with 1 to 6 carbon atoms;
$R_2$ is alkyl with 1 to 6 carbon atoms;
$R_3$ is alkyl with 1 to 6 carbon atoms;
$R_4$ is selected from one of hydrogen, alkyl with 1 to 18 carbon atoms, aryl, benzyl, ester-containing groups, carbamido-containing groups or heterocyclic alkane;
$R_5$ is selected from one of hydrogen, alkyl with 1 to 18 carbon atoms, aryl, benzyl, groups containing at least one ester group, groups containing at least one carbamido or heterocyclic alkane;
$R_4$ and $R_5$ are the same or different.

The further technical scheme is: $R_1$, $R_2$ or $R_3$ are one of straight chain alkyl with 1 to 6 carbon atoms, branched alkyl with 1 to 6 carbon atoms, cyclic alkane with 1 to 6 carbon atoms, aromatic alkyl with 1 to 6 carbon atoms or alkyl aryl with 1 to 6 carbon atoms; $R_1$, $R_2$ and $R_3$ are the same or different. According to the specific embodiment of the present invention, $R_1$, $R_2$ or $R_3$ is selected from one of methyl, ethyl, n-propyl, n-butyl, isopropyl or isobutyl. According to a more preferred embodiment of the present invention, $R_1$, $R_2$ or $R_3$ is methyl, ethyl, propyl or butyl.

The further technical scheme is: $R_4$ or $R_5$ is an ester-containing group, the group has a structure of formula (II):

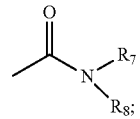

$R_6$ is alkyl with 1 to 18 carbon atoms; alkyl is selected from one of straight chain alkyl, branched alkyl, cyclic alkane, aromatic alkyl or alkyl aryl. According to a preferred embodiment of the present invention, $R_6$ is selected from one of methyl, ethyl, propyl, butyl, isopropyl, isobutyl, benzyl, dodecyl or octadecyl. According to the more preferred embodiment of the present invention, $R_6$ is selected from methyl or ethyl.

The further technical scheme is: $R_4$ or $R_5$ is an carbamido-containing group, the group has a structure of formula (III):

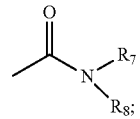

$R_7$ or $R_8$ is selected from one of hydrogen, alkyl with 1 to 18 carbon atoms, aryl or benzyl; alkyl is one of straight chain alkyl, branched alkyl, cyclic alkane, aromatic alkyl or alkyl aryl. According to the preferred embodiment of the present invention, $R_7$ or $R_8$ is selected from one of hydrogen, methyl, ethyl, n-propyl, n-butyl, isopropyl, isobutyl, aryl, benzyl or dodecyl. According to the more preferred embodiment of the present invention, $R_7$ or $R_8$ is hydrogen.

The further technical scheme is: $R_4$ or $R_5$ is a heterocycloalkane-containing group, the group has a structure of formula (IV):

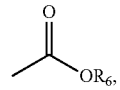

$R_9$ is alkyl with 1 to 12 carbon atoms; alkyl is one of straight chain alkyl, branched alkyl or cyclic alkane. According to the preferred embodiment of the present invention, $R_9$ is alkyl with 1 to 12 carbon atoms; alkyl is one of straight chain alkyl, branched alkyl or cyclic alkane; the alkyl chain segment contains one or more of N, O, S, carbonyl or hydroxyl. According to the preferred embodiment of the present invention, $R_4$ or $R_5$ is selected from one of pyrrole, imidazole, oxazole, piperidine, morpholine or oxazine. According to the more preferred embodiment of the present invention, $R_4$ or $R_5$ is morpholine.

The further technical scheme is: $R_4$ or $R_5$ is selected from one of hydrogen, methyl, ethyl, n-propyl, n-butyl, isopropyl, isobutyl, phenyl, benzyl, ester group, carbamido or heterocyclic alkane. According to the preferred of the present invention, $R_4$ or $R_5$ is propyl, n-butyl, ester group, carbamido or heterocyclic alkane.

In the present invention, the moisture reactive test of α-silane coupling agent is measured by the surface curing time of the polymerized α,ω-dihydroxy polysiloxane (107-silicone polymer). The method is as follows: adding the linear polymerized α,ω-dihydroxy polysiloxane (average molar mass: bout 69000 g/mol) and 2.0 equivalent of α-silane coupling agent in a rapid mixer (DAV 150 FV from Hausschild) at 2700 rpm, without metal catalysts, after mixing for 20 seconds, pouring out the resulting basic material, and testing the surface curing time by contacting the surface with a scraper at room temperature with 50±5% relative humidity.

In the present invention, specific steps of the α-silane coupling agent on silicone rubber curing speed test are: adding 700 g of the nano-silica 107 basic material and 350 g of plasticizer to the vacuum mixer, after stirring uniformly, adding 20 g of the product to be examined to the vacuum mixer, outputting rubber after mixing for 20 minutes in a moisture-free conditions, and testing the performance at room temperature with 50±5% relative humidity.

Compared with the existing technology, the present invention has the following beneficial effects:

The α-silane coupling agent of the present invention applied to silicone rubber can cure the silicone rubber without adding a catalyst, and has fast curing speed. Moreover, the α-silane coupling agent has strong reactivity, the surface curing time is less than 2 minutes, and has good stability, which can be stored stably under conditions at room temperature for 6 months, and does not easily turn yellow.

DETAILED DESCRIPTION OF THE INVENTION

The present invention will be further illustrated and described below with reference to the embodiments of the present invention.

Preparation of Raw Materials:

Preparation of Chloromethyltriethoxysilane:

Pouring 1.5 mol of anhydrous ethanol and 200 mL of petroleum ether into a 1 L three-neck boiling flask equipped with a condenser and a thermometer. After uniformly mixing, 0.5 mol of chloromethyltrichlorosilane was slowly added dropwise under nitrogen protection, the reaction temperature was controlled to be maintained at 40° C., after finishing dripping, stirring was continued for 1 hour, and heating flux was continued for 1 hour. The solvent was removed under reduced pressure and then distilled, the product of 90 to 92° C./21 mmHg was collected to obtain 101 g of colorless transparent chloromethyltriethoxysilane. The yield was 94.9%.

Preparation of Chloromethyl methoxy-ethoxy-propoxy Silane:

Pouring 0.5 mol of chloromethyltrichlorosilane and 200 mL of petroleum ether into a 1 L three-neck boiling flask equipped with a condenser and a thermometer. After uniformly mixing, 0.5 mol of anhydrous methanol solution, 0.5 mol of anhydrous ethanol solution and 0.5 mol of anhydrous propanol solution were slowly added dropwise under nitrogen protection in order, the reaction temperature was controlled to be maintained at 40° C., after finishing driping, stirring was continued for 1 hour, and heating flux was continued for 1 hour. The solvent was removed under reduced pressure and then distilled, the product of 78 to 82° C./5 mmHg was collected to obtain 95 g of colorless transparent chloromethyl methoxy-ethoxy-propoxy silane. The yield was 89.3%.

According to the above method, anhydrous methanol can be replaced by different combinations of one or more of ethanol, propanol, isopropanol, butanol or isobutanol.

Embodiment 1

Pouring 1.5 mol of n-propylamine, 0.1 g of potassium iodide and 300 mL of xylene into a 1 L reaction flask, heating the compound under nitrogen protection, when the temperature of the system was raised to 50° C., 0.5 mol of chloromethyltriethoxysilane was slowly dropped into the system, the temperature of the system was controlled at most 55° C., dropping was continued for about 1 hour, then thermostatic reaction was continued for 2 hours. After the temperature was lowered to room temperature, 300 mL of petroleum ether was added, and the resulting n-propylamine hydrochloride was filtered off. The solvent was removed under reduced pressure and then distilled, and the product of 105-110° C./5 mmHg was collected to obtain 97.7 g of colorless transparent α-n-propylamine methyltriethoxysilane. The yield was 83.1%.

Pouring 0.2 mol of α-n-propylamine methyltriethoxysilane into a 1 L three-neck boiling flask, heating the compound under nitrogen protection, when the temperature was raised to 100° C., 0.25 mol of dimethyl-carbonate was slowly dropped into the system of α-n-propylamine methyltriethoxysilane, after finishing dripping, thermostatic reaction was continued for 2 hours. The low-boiling residue was removed under reduced pressure and then distilled, and the product of 140 to 142° C./4 mmHg was collected to obtain 44.1 g of colorless transparent N-n-propyl-N-carbomethoxy-aminomethyl triethoxysilane solution. The yield was 75.1%.

$^1$H NMR (300 MHz, CDCl$_3$), δ3.60 (9H), 2.53 (2H), 2.14 (2H), 1.46 (2H), 0.87 (12H)

Elemental analysis: C % 49.08, H % 9.23, N % 4.80.

Embodiment 2

Pouring 1.5 mol of n-butylamine, 0.1 g of potassium iodide and 300 mL of xylene into a 1 L reaction flask, heating the compound under nitrogen protection, when the temperature of the system was raised to 50° C., 0.5 mol of chloromethyltriethoxysilane was slowly dropped into the system, the temperature of the system was controlled at 55° C. or less, dropping was continued for about 1 hour, then thermostatic reaction was continued for 2 hours. After the temperature was lowered to room temperature, 300 mL of petroleum ether was added, and the resulting n-butylamine hydrochloride was filtered off. The solvent was removed under reduced pressure and then distilled, and the product of 108-116° C./5 mmHg was collected to obtain 100.0 g of colorless transparent α-n-butyl amine methyltriethoxysilane. The yield was 80.3%.

Pouring 0.2 mol of α-n-butylamine methyltriethoxysilane into a three-neck boiling flask, heating the compound under nitrogen protection, when the temperature was raised to 105° C., 0.25 mol of dimethyl-carbonate was slowly dropped into the system of α-n-butylamine methyltriethoxysilane, after finishing dripping, thermostatic reaction was continued for 2 hours. The low-boiling residue was removed under reduced pressure and then distilled, and the product of 148 to 152° C./5 mmHg was collected to obtain 46.8 g of colorless transparent N-n-butyl-N-carbomethoxy-aminomethyl triethoxysilane solution. The yield was 76.3%.

$^1$H NMR (300 MHz, CDCl$_3$), δ3.64 (9H), 2.63 (2H), 2.16 (2H), 1.52 (m, 2H), 1.28 (2H), 0.87 (m, 12H)

Elemental analysis: C % 50.52, H % 9.54, N % 4.53.

Embodiment 3

Pouring 1.5 mol of n-propylamine, 0.1 g of potassium iodide and 300 mL of xylene into a 1 L reaction flask, heating the compound under nitrogen protection, when the temperature of the system was raised to 50° C., 0.5 mol of chloromethyltrimethoxysilane was slowly dropped into the system, the temperature of the system was controlled at 55° C. or less, dropping was continued for 1 hour, then thermostatic reaction was continued for 2 hours. After the temperature was lowered to room temperature, 300 mL of petroleum ether was added, and the resulting n-propylamine hydrochloride was filtered off. The solvent was removed under reduced pressure and then distilled, and the product of 105-110° C./5 mmHg was collected to obtain 82.4 g of colorless transparent α-n-propylamine methyltrimethoxysilane. The yield was 85.4%.

Pouring 0.2 mol of α-n-propylamine methyltrimethoxysilane into a three-neck boiling flask, heating the compound under nitrogen protection, when the temperature was raised to 100° C., 0.25 mol of dimethyl-carbonate was slowly dropped into the system of α-n-propylamine methyltrimethoxysilane, after finishing driping, thermostatic reaction was continued for 2 hours. The low-boiling residue was removed under reduced pressure and then distilled, and the product of 130 to 135° C./5 mmHg was collected to obtain 40.3 g of colorless transparent N-n-propyl-N-carbomethoxy-aminomethyl trimethoxysilane solution. The yield was 80.3%.

$^1$H NMR (300 MHz, CDCl$_3$), δ3.68 (12H), 2.57 (2H), 2.18 (2H), 1.42 (2H), 0.89 (3H)

Elemental analysis: C % 42.93, H % 8.44, N % 5.60.

Embodiment 4

Pouring 1.5 mol of n-propylamine, 0.1 g of potassium iodide and 300 mL of xylene into a 1 L reaction flask, heating the compound under nitrogen protection, when the temperature of the system was raised to 50° C., 0.5 mol of chloromethyl methoxyethoxypropoxysilane was slowly dropped into the system, the temperature of the system was controlled at 60° C. or less, dropping was continued for about 1 hour, then thermostatic reaction was continued for 2 hours. After the temperature was lowered to room temperature, 300 mL of petroleum ether was added, and the resulting n-propylamine hydrochloride was filtered off. The solvent was removed under reduced pressure and then distilled, and the product of 109-115° C./5 mmHg was collected to obtain 93.1 g of colorless transparent α-n-propylamine methy methoxyethoxypropoxysilane. The yield was 79.2%.

Pouring 0.2 mol of α-n-propylamine methy methoxyethoxypropoxysilane into a three-neck boiling flask, heating the compound under nitrogen protection, when the temperature was raised to 105° C., 0.25 mol of dimethyl-carbonate was slowly dropped into the system of α-n-propylamine methy methoxyethoxypropoxysilane, after finishing driping, thermostatic reaction was continued for 2 hours. The low-boiling residue was removed under reduced pressure and then distilled, and the product of 138 to 145° C./5 mmHg was collected to obtain 41.5 g of colorless transparent N-n-propyl-N-carbomethoxy-aminomethyl methoxyethoxypropoxysilane. The yield was 70.7%.

$^1$H NMR (300 MHz, CDCl$_3$), δ3.75 (10H), 2.62 (2H), 2.18 (2H), 1.50 (4H), 0.93 (9H)

Elemental analysis: C % 49.15, H % 9.30, N % 4.73.

Embodiment 5

Pouring 0.2 mol of α-n-propylamine methyltriethoxysilane into a three-neck boiling flask, heating the compound under nitrogen protection, when the temperature was raised to 100° C., 0.25 mol of diethyl-carbonate was slowly dropped into the system of α-n-propylamine methyltriethoxysilane, after finishing dripping, thermostatic reaction was continued for 2 hours. The low-boiling residue was removed under reduced pressure and then distilled, and the product of 144 to 148° C./4 mmHg was collected to obtain 44.3 g of colorless transparent N-n-propyl-N-carboethoxy-aminomethyl triethoxysilane solution. The yield was 72.1%.

$^1$H NMR (300 MHz, CDCl$_3$), δ3.54 (8H), 2.51 (2H), 2.13 (2H), 1.46 (2H), 0.91 (15H)

Elemental analysis: C % 50.74, H % 9.48, N % 4.54.

Embodiment 6

Pouring 0.2 mol of α-n-propylamine methyltriethoxysilane and 0.25 mol of carbamide into a three-neck boiling flask, heating the compound under nitrogen protection, when the temperature was raised to 100° C., thermostatic reaction was continued for 2 hours. The low-boiling residue was removed under reduced pressure and then distilled, and the product of 175 to 185° C./5 mmHg was collected to obtain 42.2 g of colorless transparent N-n-propyl-N-carbamido-aminomethyl triethoxysilane solution. The yield was 75.8%.

$^1$H NMR (300 MHz, MeOD), δ6.2 (2H), 3.75 (6H), 2.78 (2H), 2.33 (2H), 1.53 (2H), 0.94 (12H)

Elemental analysis: C % 47.43, H % 9.43, N % 10.12.

Embodiment 7

Pouring 1.5 mol of morpholine, 0.1 g of potassium iodide and 300 mL of xylene into a 1 L reaction flask, heating the compound under nitrogen protection, when the temperature of the system was raised to 50° C., 0.5 mol of chloromethyltrimethoxysilane was slowly dropped into the system, the temperature of the system was controlled at 55° C. or less, dropping was continued for about 1 hour, then thermostatic reaction was continued for 2 hours. After the temperature was lowered to room temperature, 300 mL of petroleum ether was added, and the resulting amine salt was filtered off. The solvent was removed under reduced pressure and then distilled, and the product of 99-103° C./5 mmHg was collected to obtain 96 g of colorless transparent α-morpholine methyltrimethoxysilane. The yield was 86.8%.

$^1$H NMR (300 MHz, CDCl$_3$), δ3.65 (4H), 3.52 (6H), 2.49 (4H), 1.96 (2H), 0.90 (9H) Elemental analysis: C % 50.12, H % 9.60, N % 5.29.

Embodiment 8

Pouring 1.5 mol of morpholine, 0.1 g of potassium iodide and 300 mL of xylene into a 1 L reaction flask, heating the compound under nitrogen protection, when the temperature of the system was raised to 50° C., 0.5 mol of chloromethyltriethoxysilane was slowly dropped into the system, the temperature of the system was controlled at 55° C. or less, dropping was continued for about 1 hour, then thermostatic reaction was continued for 2 hours. After the temperature was lowered to room temperature, 300 mL of petroleum ether was added, and the resulting amine salt was filtered off. The solvent was removed under reduced pressure and then distilled, and the product of 105-108° C./5 mmHg was collected to obtain 96 g of colorless transparent α-morpholine methyltriethoxysilane. The yield was 85.4%.

$^1$H NMR (300 MHz, CDCl$_3$), δ3.64 (4H), 3.54 (9H), 2.49 (4H), 1.94 (2H)

Elemental analysis: C % 43.38, H % 8.62, N % 6.31.

Embodiment 9

The α-silane coupling agents obtained in embodiments 1-8 with commercially available N, N-diethylaminomethyltriethoxysilane (ND-22), anilinomethyltriethoxysilane (ND-42) were stored in a glass bottle at room temperature respectively to obtain 10 samples, the storage stability of each sample was examined, the results were shown in table 1.

TABLE 1

α-silane coupling stability comparison

| No. | 0 month | 3 months | 6 months | 12 months |
|---|---|---|---|---|
| embodiment1 | colorless transparent | colorless transparent | colorless transparent | colorless transparent |
| embodiment 2 | colorless transparent | colorless transparent | colorless transparent | colorless transparent |
| embodiment 3 | colorless transparent | colorless transparent | colorless transparent | colorless transparent |
| embodiment 4 | colorless transparent | colorless transparent | colorless transparent | colorless transparent |
| embodiment 5 | colorless transparent | colorless transparent | colorless transparent | colorless transparent |
| embodiment 6 | colorless transparent | colorless transparent | colorless transparent | colorless transparent |
| embodiment 7 | colorless transparent | colorless transparent | light yellow | redish-brown |
| embodiment 8 | colorless transparent | colorless transparent | light yellow | redish-brown |
| ND-22 | colorless transparent | light yellow | redish-brown | redish-brown |
| ND-42 | colorless transparent | redish-brown | redish-brown | redish-brown |

Embodiment 10

The α-silane coupling agents obtained in embodiments 1-8 with commercially available N, N-diethylaminomethyltriethoxysilane (ND-22), anilinomethyltriethoxysilane (ND-42) and methyl trimethoxy (TMO) silane were used in silicone rubber respectively to obtain 11 samples, the surface curing time and cured depth of each sample were measured according to the procedures described in the summary of the present invention, the results were shown in Table 2.

TABLE 2

The properties comparative data of different cross-linking agent

| Performance Embodiment | Surface Curing Time | Cured Depth | | |
|---|---|---|---|---|
| | | 8 h | 24 h | 72 h |
| Embodiment 1 | 20 s | 1.98 mm | 2.50 mm | 4.60 mm |
| Embodiment 2 | 30 s | 1.92 mm | 2.43 mm | 4.52 mm |
| Embodiment 3 | 8 s | 1.52 mm | 2.05 mm | 3.21 mm |
| Embodiment 4 | 2 min | 2.18 mm | 2.68 mm | 4.93 mm |
| Embodiment 5 | 40 s | 1.95 mm | 2.48 mm | 4.54 mm |
| Embodiment 6 | 14 s | 1.85 mm | 2.27 mm | 4.40 mm |
| Embodiment 7 | 10 s | 1.48 mm | 2.08 mm | 3.30 mm |
| Embodiment 8 | 25 s | 1.58 mm | 2.21 mm | 4.23 mm |
| ND-22 | 6 min | 1.84 mm | 2.37 mm | 4.33 mm |
| ND-42 | 40 min | 1.78 mm | 2.26 mm | 4.28 mm |
| TMO | non-curing | — | — | — |

Although the present invention has been described herein with reference to the illustrative embodiments of the present invention, the above embodiments are merely preferred embodiments of the present invention, and the scope of the present invention is not limited to the above embodiments, and it should be understood that the technician in this field can design many other modifications and embodiments, such modifications and embodiments derived from the spirit of the present invention will fall within the scope and spirit of the principles disclosed in this application.

What is claimed is:

1. An α-silane coupling agent, represented by a structure formula of formula (I):

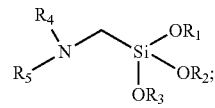

wherein R$_1$ is ethyl;
R$_2$ is ethyl;
R$_3$ is ethyl;
R$_4$ is n-butyl; and
R$_5$ is carbomethoxy.

2. An α-silane coupling agent used in the curing process of sealant, wherein the α-silane coupling agent, represented by a structure formula of formula (I):

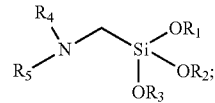

wherein R$_1$ is ethyl;
R$_2$ is ethyl alkyl with 1 to 6 carbon atoms;
R$_3$ is ethyl;
R$_4$ is n-butyl; and
R$_5$ is carbomethoxy.

* * * * *